(12) United States Patent
Ren et al.

(10) Patent No.: US 10,269,989 B2
(45) Date of Patent: Apr. 23, 2019

(54) WATER-INSENSITIVE GAS SENSOR USING POLYMER-ENCAPSULATED PT—ALGAN/GAN DIODES

(71) Applicant: University of Florida Research Foundation, Incorporated, Gainesville, FL (US)

(72) Inventors: Fan Ren, Gainesville, FL (US); Stephen J. Pearton, Gainesville, FL (US); Soohwan Jang, Gainesville, FL (US); Sunwoo Jung, Suwon-si (KR)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 15/906,701

(22) Filed: Feb. 27, 2018

(65) Prior Publication Data

US 2018/0248048 A1    Aug. 30, 2018

Related U.S. Application Data

(60) Provisional application No. 62/464,542, filed on Feb. 28, 2017.

(51) Int. Cl.
*G01N 27/12* (2006.01)
*G01N 33/00* (2006.01)
(Continued)

(52) U.S. Cl.
CPC ......... *H01L 29/872* (2013.01); *G01N 27/129* (2013.01); *G01N 27/4074* (2013.01);
(Continued)

(58) Field of Classification Search
CPC .............. G01N 33/005; G01N 27/129; G01N 27/4074; H01L 29/872; H01L 29/47; H01L 21/0495; H01L 29/66143; H01L 29/66212
See application file for complete search history.

(56) References Cited

U.S. PATENT DOCUMENTS

2005/0221628 A1\* 10/2005 Tanaka ................ H01L 29/2003
438/791
2006/0115640 A1\* 6/2006 Yodh ...................... B82Y 10/00
428/221

(Continued)

OTHER PUBLICATIONS

Astbury et al., "Spontaneous ignition of hydrogen leaks: a review of postulated mechanisms," International Journal of Hydrogen Energy, Sep. 2007, pp. 1-12.

(Continued)

*Primary Examiner* — Ngan V Ngo
(74) *Attorney, Agent, or Firm* — Alston & Bird LLP

(57) ABSTRACT

A hydrogen sensor can include a substrate, an Ohmic metal disposed on the substrate, a nitride layer disposed on the substrate and having a first window exposing the substrate, a Schottky metal placed in the first window and disposed on the substrate, a final metal disposed on the nitride layer and the Schottky metal and having a second window exposing the Schottky metal, and a polymethyl-methacrylate (PMMA) layer encapsulating the second window. The PMMA layer can fill the second window and be in contact with the Schottky metal.

13 Claims, 12 Drawing Sheets

(51) Int. Cl.
*H01L 21/04* (2006.01)
*H01L 23/29* (2006.01)
*H01L 23/31* (2006.01)
*H01L 29/20* (2006.01)
*H01L 29/47* (2006.01)
*H01L 29/66* (2006.01)
*G01N 27/407* (2006.01)
*H01L 29/205* (2006.01)
*H01L 29/872* (2006.01)

(52) U.S. Cl.
CPC ....... *G01N 33/005* (2013.01); *H01L 21/0495* (2013.01); *H01L 23/291* (2013.01); *H01L 23/293* (2013.01); *H01L 23/3171* (2013.01); *H01L 23/3192* (2013.01); *H01L 29/2003* (2013.01); *H01L 29/205* (2013.01); *H01L 29/47* (2013.01); *H01L 29/475* (2013.01); *H01L 29/66143* (2013.01); *H01L 29/66212* (2013.01); *H01L 29/66219* (2013.01)

(56) References Cited

U.S. PATENT DOCUMENTS

2011/0088456 A1* 4/2011 Ren .................. G01N 33/005 73/31.06
2011/0197657 A1* 8/2011 Gole .................. G01N 27/021 73/31.05

OTHER PUBLICATIONS

Hung et al., "SnO2 functionalized AlGaN/GaN high electron mobility transistor for hydrogen sensing applications," International Journal of Hydrogen Energy, Sep. 2012, pp. 13783-13788, vol. 37.

Matsuo et al., "Pt schottky diode gas sensors formed on GaN and AlGaN/GaN heterostructure," Applied Surface Science, May 2005, pp. 273-276, vol. 244.

Hasegawa et al., "Hydrogen sensing characteristics and mechanism of Pd/AlGaN/GaN schottky diodes subjected to oxygen gettering," Journal of Vacuum Science and Technology B, Jul. 2007, pp. 1495-1503, vol. 25, No. 4.

Lim et al., "Room temperature hydrogen detection using Pd-coated GaN nanowires," Applied Physics Letters, Aug. 2008, pp. 1-3, vol. 93, No. 072109.

Irokawa, "Hydrogen interaction with GaN metal-insulator-semiconductor diodes," Physica B, Aug. 2012, pp. 2957-2959, vol. 407.

Liu et al., "On the voltage dependence of sensitivity for schottky-type gas sensor," Applied Physics Letters, Dec. 2014, pp. 1-4, vol. 105, No. 223503.

Yu et al., "Wireless hydrogen sensor network using AlGaN/GaN high electron mobility transistor differential diode sensors," Sensors and Actuators B: Chemical, Dec. 2008, pp. 188-194, vol. 135.

Zhong et al., "Comparative study of schottky diode type hydrogen sensors based on a honeycomb GaN nanonetwork and on a planar GaN film," International Journal of Hydrogen Energy, May 2014, pp. 8564-8575, vol. 39.

Tsai et al., "Hydrogen sensing properties of a Pt-oxide-GaN schottky diode," Journal of Applied Physics, Jul. 2008, pp. 1-6, vol. 104, No. 024515.

Lo et al., "Effect of humidity on hydrogen sensitivity of Pt-gated AlGaN/GaN high electron mobility transistor based sensors," Applied Physics Letters, Jun. 2010, pp. 1-3, vol. 96, No. 232106.

Das et al., "Simplified gas sensor model based on AlGaN/GaN heterostructure schottky diode," AIP Conference Proceedings, Aug. 2015, pp. 1-4, vol. 1675, No. 020014.

Hong et al., "A highly sensitive hydrogen sensor with gas selectivity using a PMMA membrane-coated Pd nanoparticle/single-layer graphene hybrid," ACS Applied Materials and Interfaces, Jan. 2015, pp. 3554-3561, vol. 7.

Baik et al., "Hydrogen sensing characteristics of semipolar (1122) GaN schottky diodes," Applied Physics Letters, Feb. 2014, pp. 1-3, vol. 104, No. 072103.

Kim et al., "Highly sensitive AlGaN/GaN diode-based hydrogen sensors using platinum nanonetworks," Sensors and Actuators B: Chemical, Mar. 2012, pp. 64-68, vol. 164.

Kim et al., "AlGaN/GaN HEMT based hydrogen sensor with platinum nanonetwork gate electrode," Current Applied Physics, Oct. 2013, pp. 1746-1750, vol. 13.

Lo, C. F., Et Al., "Effect of humidity on hydrogen sensitivity of Pt-gated AlGaN/GaN high electron mobility transistor based sensors", *Applied Physics Letters*, 2010, pp. 232106-1 thru 232106-3, vol. 96, American Institute of Physics, U.S.A.

* cited by examiner

WATER-INSENSITIVE GAS SENSOR USING POLYMER-ENCAPSULATED PT—ALGAN/GAN DIODES

CROSS-REFERENCE TO RELATED APPLICATION

This application claims the benefit of U.S. Provisional Application Ser. No. 62/464,542, filed Feb. 28, 2017, which is incorporated herein by reference in its entirety, including any figures, tables, and drawings.

STATEMENT OF GOVERNMENT SUPPORT

This invention was made with government support under grant number HDTRA1-11-1-0020 awarded by the U.S. Department of Defense, Defense Threat Reduction Agency (DOD/DTRA). The government has certain rights in the invention.

BACKGROUND

There is currently great interest in hydrogen as an emission-free fuel for automobiles to both increase fuel economy and decrease vehicle emissions [1]-[3]. It is expected that hydrogen can become a major energy supply in many applications, including transportation, central and distributed electric power, portable power, and combined heat and power for buildings and industrial processes [2], [3]. Because hydrogen gas is extremely reactive with oxygen and has low ignition energy, it is prone to spontaneous flammable ignition. It is therefore critically important that robust and fast hydrogen gas detection technologies be available to ensure safe handling [1]-[3].

BRIEF SUMMARY

Embodiments of the subject invention provide novel and advantageous hydrogen sensors that are encapsulated (e.g., by polymethyl-methacrylate (PMMA)), thereby allowing the hydrogen to pass through and inhibiting water from passing through.

In an embodiment, a hydrogen sensor can comprise a substrate, an Ohmic metal disposed on the substrate, a nitride layer disposed on the substrate and having a first window exposing the substrate, a Schottky metal placed in the first window and disposed on the substrate, a final metal disposed on the nitride layer and the Schottky metal and having a second window exposing the Schottky metal, and an encapsulation layer (e.g., a PMMA layer) encapsulating the second window.

In another embodiment, a Schottky diode can comprise a substrate, an Ohmic metal disposed on an Ohmic contact area of the substrate, a nitride layer disposed on the substrate and having a window exposing a Schottky contact area of the substrate, a Schottky metal disposed on the Schottky contact area of the substrate, a final metal connected to the Schottky metal, and a polymer encapsulant directly disposed on the Schottky metal.

In yet another embodiment, a method for manufacturing a hydrogen sensor can comprise providing a substrate, forming an Ohmic metal on an Ohmic contact area of the substrate, depositing a $SiN_x$ layer on the substrate and the Ohmic layer, forming a first window exposing a Schottky contact area of the substrate by removing the $SiN_x$ layer on the substrate, forming a Schottky metal on the Schottky contact area of the substrate, forming a final metal on the Schottky metal, and forming an encapsulation layer (e.g., a PMMA layer) encapsulating the Schottky metal.

DETAILED DESCRIPTION

Figure 1:
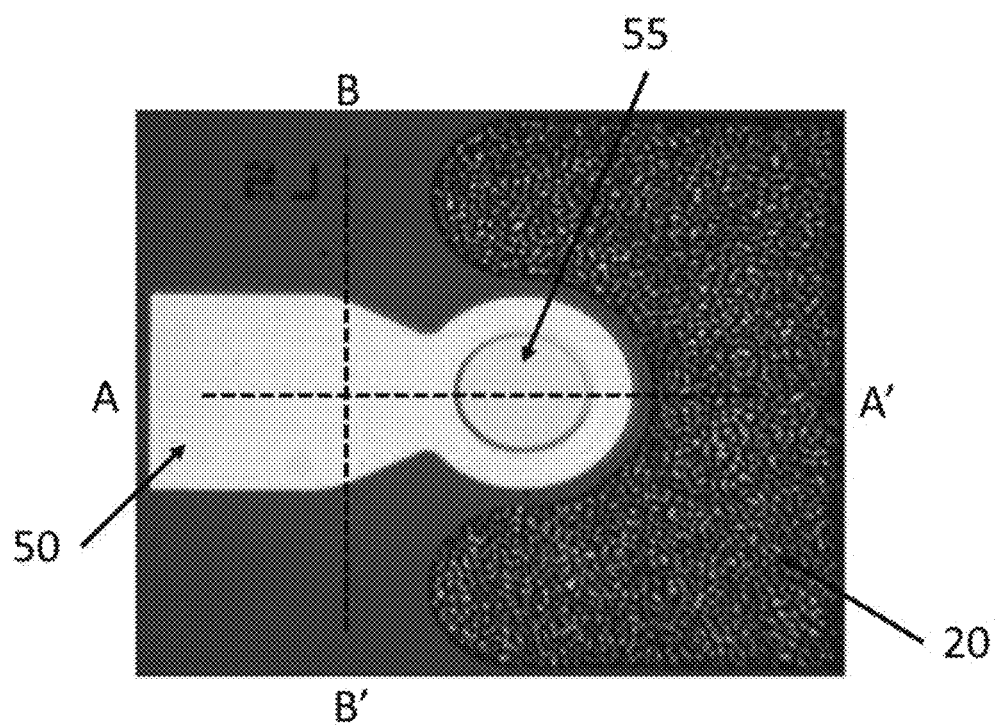
FIG. 1 shows an optical microscope image of a hydrogen sensor according to an embodiment of the subject invention.

Embodiments of the subject invention provide novel and advantageous hydrogen sensors using an encapsulated (e.g., polymethyl-methacrylate (PMMA)-encapsulated) Schottky diode that inhibit water from passing through an encapsulating layer (e.g., a PMMA encapsulating layer) and allow hydrogen to pass through the encapsulating layer.

There has been a strong need for robust hydrogen sensors to monitor leaks in applications where hydrogen is produced or utilized, such as hydrogen-fueled vehicles, aircraft, fuel cells, and industrial processes. Among semiconductor-based hydrogen sensors, there has been significant work on the use of Pt- or Pd-gate metals on GaN-based diodes, which have been shown to be capable of selectively detecting low concentrations of hydrogen at room temperature. In particular, low concentration detection is valuable because hydrogen is combustible when its concentration in the air reaches or exceeds 4.65% [3], [30]. The hydrogen response mechanism of GaN Schottky diodes involves hydrogen molecule dissociation to atomic form during diffusion through the catalytic Pd or Pt metal to form an adsorbed dipole layer at the metal-semiconductor interface. This hydrogen-induced dipole layer causes a reduction of the effective Schottky barrier height, leading to an increase in the sensing current at fixed applied bias voltage.

Among semiconductor-based hydrogen sensors, various types of GaN thin film or nanostructured devices contacted with Pt- or Pd-gate metals are attractive for their robustness and wide operating temperature. In addition, the availability of piezoelectric AlGaN/GaN heterostructures enables the design of transistor-based sensors with enhanced sensitivity. These devices have low concentration detection sensitivities (hundreds of parts per million (ppm) at room temperature), which is well below the concentration at which hydrogen is combustible in the air (4.65%). The role of the catalytic metal is to dissociate molecular hydrogen to atomic form, leading to an adsorbed dipole layer at the metal-semiconductor interface. This leads to a reduction of the Schottky barrier height, which in turn modulates the current flowing in the device at a fixed operating voltage.

Recent innovations have increased the detection sensitivities in AlGaN/GaN-based hydrogen sensing, including the (i) use of catalytically active Pt nano-networks on the gate, (ii) surface roughening of the active area using photoelectrochemical etching to increase the density of available adsorption sites, and (iii) using different orientations and surface polarities. In the latter case, it has been observed that semipolar and c-plane N-polar GaN have much different responses compared to conventional c-plane Ga-face GaN due to the different affinities of hydrogen for the different atomic planes and polarities. A remaining issue with AlGaN/GaN hydrogen sensors is the fact that their sensitivity is significantly degraded in the presence of humidity or water. This limits their practical application, and methods to mitigate the effects of absorbed water and oxygen molecules would be a major step towards expanding these applications.

In an embodiment of the subject invention, the encapsulation with a common polymer film, such as a PMMA layer used in the semiconductor industry as a component of electron beam resists, attenuates or eliminates this problem. The PMMA has a low permeability coefficient for moisture. Given the ease with which it can be spun-on to a surface and patterned, this makes it an attractive candidate as a moisture barrier on GaN-based hydrogen sensors.

With respect to the biggest issue with GaN-based hydrogen sensors, sensitivity to humidity in the ambient, an encapsulated Pt—AlGaN/GaN Schottky diode fabricated on c-plane layers grown on sapphire with PMMA provides effective mitigation of the effects of water. Without PMMA encapsulation, the absolute current signal for detection of 500 ppm of $H_2$ is decreased by a factor of 8 in the presence of water. By sharp contrast, encapsulated diodes show no decrease in response in the presence of water. The relative current changes are of the order $2.8 \times 10^5$% when 500 ppm $H_2$ is introduced to the surface of bare or PMMA encapsulated diodes in the absence of water or to encapsulated diodes in the presence of water. Detection limits of ~150 ppm $H_2$ (0.015% by volume) were obtained with standard forward bias detection mode at 1.3V. These diodes show no physical degradation or loss of sensitivity when repeatedly cycled (50×, 1 min hold at each temperature) between 25-100° C. There is complete selectivity for hydrogen sensing over other gases, including CO, $CO_2$, $NO_2$, $O_2$ and $CH_4$. The PMMA encapsulation provides an effective and robust barrier to moisture, greatly increasing the range of environments in which the sensors can be used. The technology of embodiments of the subject invention can also be used for ethanol, ammonia, methane, phenol, and other volatile organic compounds (VOCs). In addition to or instead of PMMA, other materials can be used, including but not necessarily limited to polyimide, polycarbonate, benzocyclobutene (BCB), and combinations thereof.

The encapsulation (e.g., with PMMA) according to embodiments of the subject invention provides a robust means of eliminating the sensitivity to moisture of the AlGaN/GaN hydrogen sensors. In addition, the encapsulated devices suffer no change in hydrogen detection sensitivity in the presence of moisture, and the devices can be repeatedly cycled to temperatures up to 100° C. without any change in characteristics.

FIG. 1 shows an optical microscope image of a hydrogen sensor according to an embodiment of the subject invention. Referring to FIG. 1, the hydrogen sensor can comprise a Schottky diode including an Ohmic metal 20 and a final metal 50 for detecting current, and a second window 55 provided adjacent the final metal 50 for receiving hydrogen. The hydrogen passing through the second window 55 affects the current of the Schottky diode and the hydrogen sensor detects the hydrogen by detecting a change in the current.

Figure 2A:
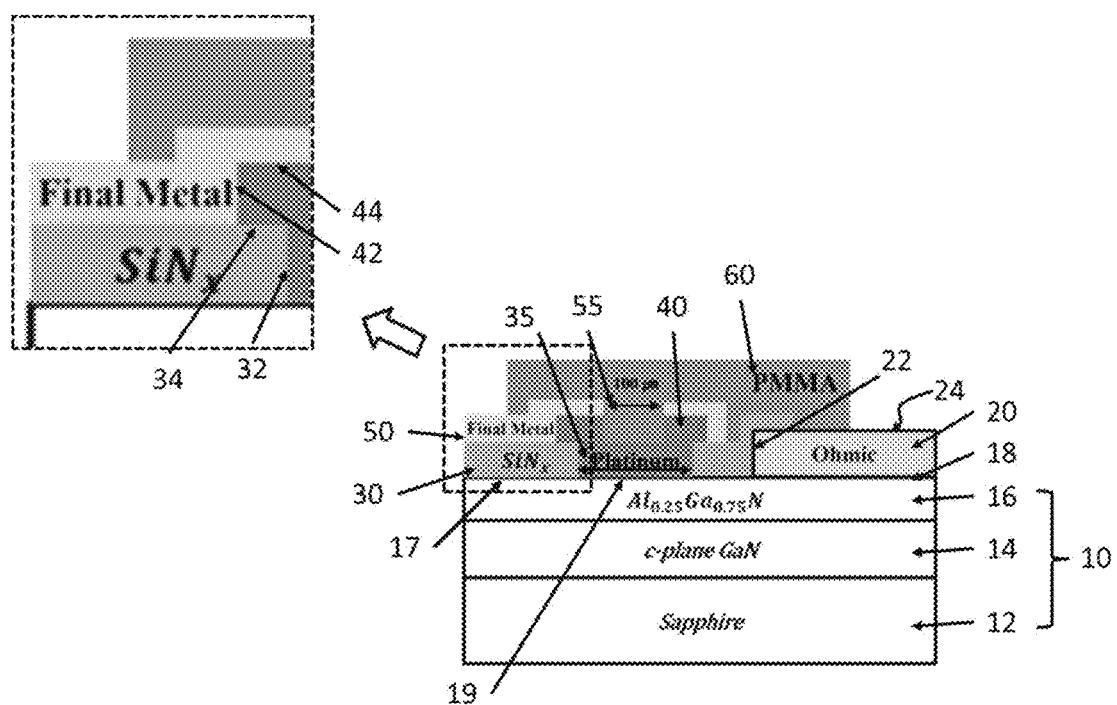
FIG. 2(a) shows a cross-sectional view taken along line A-A' in FIG. 1, of a hydrogen sensor according to an embodiment of the subject invention.
Figure 2B:
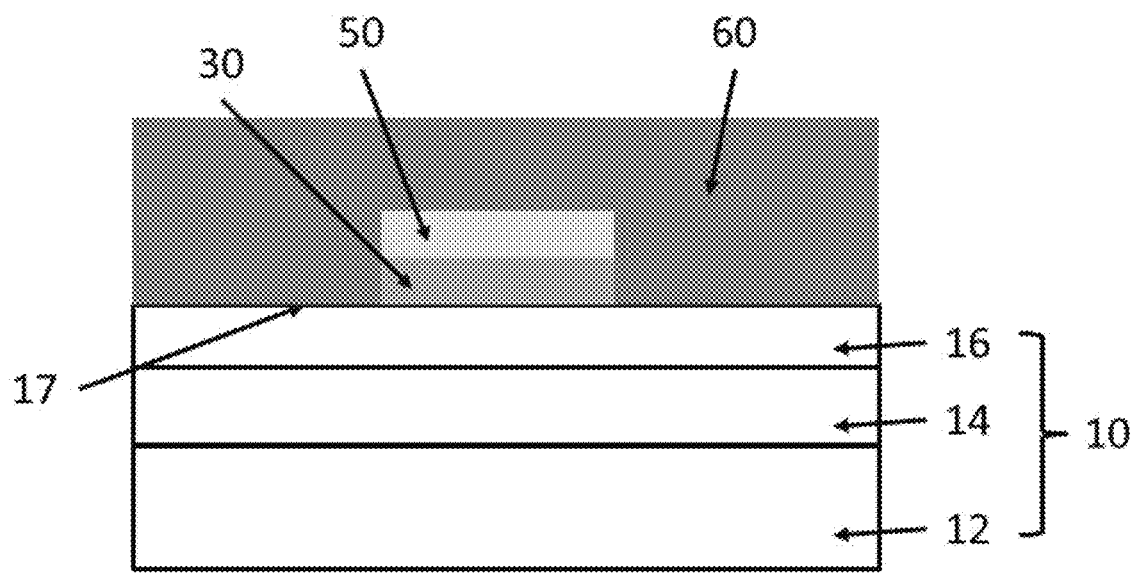
FIG. 2(b) shows a cross-sectional view taken along line B-B' in FIG. 1, of a hydrogen sensor according to an embodiment of the subject invention.

FIG. 2(a) shows a cross-sectional view taken along line A-A' in FIG. 1 and FIG. 2(b) shows a cross-sectional view taken along line B-B' in FIG. 1. Referring to FIGS. 2(a) and 2(b), the hydrogen sensor can comprise a Schottky diode including a substrate 10 comprising a sapphire layer 12, a GaN layer 14 on the sapphire layer 12, and an AlGaN layer 16 on the GaN layer 14. Instead of the sapphire layer 12, the GaN layer 14 and the AlGaN layer 16 can be formed on a silicon layer, a SiC layer, or other suitable material. The sapphire layer 12 has c-plane, and the GaN layer 14 disposed on the sapphire layer 12 is formed as a c-plane GaN layer. The AlGaN layer 16 can be expressed as an $Al_xGa_{1-x}N$ layer, where x is in a range of 0 to 1 and can be preferably 0.25 or 0.3, but embodiments of the subject invention are not limited to a particular number.

An Ohmic metal 20 and a Schottky metal 40 can be disposed on a top surface 17 of the substrate 10 for the Schottky diode. In a particular embodiment, the Ohmic metal 20 is disposed on an Ohmic contact area 18 of the top surface 17 to make an Ohmic contact between the substrate 10 and the Ohmic metal 20, and the Schottky metal 40 is disposed on a Schottky contact area 19 of the top surface 17 to make a Schottky contact between the substrate 10 and the Schottky metal 40. The Ohmic metal 20 can include a Ti layer, an Al layer, a Ni layer, and/or an Au layer, and the Schottky metal 40 can include Platinum (Pt), though embodiments are not limited thereto.

A nitride layer 30 can be disposed on the top surface 17 except the Ohmic contact area 18 and the Schottky contact area 19. That is, the nitride layer 30 can provide a first window 35 for the Schottky metal 40 such that the Schottky metal 40 passes through the first window 35 and is in contact with the Schottky contact area 19 of the substrate 10. The nitride layer 30 adjacent to the Ohmic metal 20 can cover a part of the Ohmic metal 20 such that the nitride layer 30 is in contact with an Ohmic side surface 22 and an Ohmic top surface 24; thus, the nitride layer 30 can electrically isolate the Schottky metal 40 from the Ohmic metal 20. In addition, the Schottky metal 40 can cover a part of the nitride layer 30 such that the Schottky metal 40 is in contact with a nitride side surface 32 and a nitride top surface 34. The nitride layer 30 can be formed by a SiN$_x$ layer, though embodiments are not limited thereto.

A final metal 50 can be disposed on the nitride layer 30 and the Schottky metal 40. The final metal 50 can be spaced apart from the substrate 10 by the nitride layer 30 and can be connected to the Schottky metal 40. The final metal 50 can be in contact with a Schottky side surface 42 and a Schottky top surface 44, thereby allowing a current to flow from the Schottky metal 40 to the final metal 50. The final metal 50 can provide a second window 55 exposing the Schottky metal 40 such that hydrogen passes through the second window 55 and is in contact with the Schottky metal 40. The second window 55 can correspond to the first window 35 exposing the Schottky contact area 19, wherein a width the second window 55 can be smaller than that of the first window 35 and the width of the second window 55 can be, for example, 100 μm.

An encapsulation layer (which will be referred to for convenience as a PMMA layer, but could be a different material as discussed herein) 60 can be disposed on the final metal 50, the nitride layer 30, and the Ohmic metal 20. In addition, the PMMA layer 60 can cover the second window 55 of the final metal 50, thereby encapsulating the Schottky metal 40. The PMMA layer 60 can be placed in the second window 55 and can be in contact with the Schottky metal 40. Referring to FIG. 2(b), the PMMA layer 60 can be directly disposed on the top surface 17 in which the nitride layer 30 and the final metal 50 do not exist. Referring to FIGS. 2(a) and 2(b), the PMMA layer 60 can cover the hydrogen sensor except a part of the final metal 50 and a part of the Ohmic metal 20 for probing or bonding. The PMMA layer 60 is permeable to hydrogen but impermeable to water, thereby inhibiting water from contacting the Schottky metal 40 and maintaining the capability of the Schottky metal 40 to detect hydrogen.

The hydrogen sensor as set forth above can be manufactured by a Schottky diode manufacturing process including, for example, chemical vapor deposition and e-beam deposition.

The AlGaN/GaN HEMT layer structure including the GaN layer 14 and the AlGaN layer 16 can be grown on a c-plane sapphire layer 12 by metal organic chemical vapor deposition (MOCVD). Each of the GaN layer 14 and the AlGaN layer 16 can be an epi-layer, and the epi-layer structures can comprise a (2-μm thick) undoped GaN buffer layer followed by a (35-nm) unintentionally doped Al$_{0.3}$Ga$_{0.7}$N layer. Sheet resistances of 350 ohm/square, sheet carrier concentrations of $1.06 \times 10^{13}$ cm$^2$, and mobilities of 1900 cm$^2$/V-s can be obtained from Hall measurements. The Ohmic metal 20 of Ti/Al/Ni/Au can be formed by e-beam evaporator and lift-off, and annealed at 850° C. for 1 minute under a N$_2$ ambient. In another embodiment, the AlGaN/GaN layer can be grown on a c-plane Al$_2$O$_3$ substrate, and the AlGaN layer can be an Al$_{0.25}$Ga$_{0.75}$N layer. In addition, the Ohmic metal 20 can be formed by e-beam depositing Ti (200 Å)/Al (800 Å)/Ni (400 Å)/Au (800 Å), subsequently annealed at 900° C. for 60 seconds under a flowing N$_2$ ambient. The Ohmic metal 20 can comprise any of Ti/Alu, Ti/Al/Pt/Au, and Ti/Al/W/Au.

A (200-nm) SiN$_x$ layer can be deposited for diode isolation by plasma enhanced chemical vapor deposition (PECVD). The SiN$_x$ layer deposition can be performed at 300° C. The first window 35 for active area opening (e.g., the Schottky contact area 19) can be achieved by buffered oxide etchant (BOE) etching. A (10-nm) film (e.g., Pt film) can be deposited on the Schottky contact area 19 by e-beam evaporation.

Ti/Au based contact pads for final metal 50 can be deposited for probing and wire bonding. The Ti layer (e.g., in a thickness of 200 Å) and the Au layer (e.g., in a thickness of 2000 Å) can be formed by e-beam deposition for interconnection contacts.

The PMMA can be spun to form 200 nm of the PMMA layer 60 as a moisture barrier on some devices and opened up for contact holes for probing on the contact regions through the PMMA layer 60.

The subject invention includes, but is not limited to, the following exemplified embodiments.

Embodiment 1

A hydrogen sensor, comprising:
a substrate;
an Ohmic metal disposed on the substrate;
a nitride layer disposed on the substrate and having a first window exposing the substrate;
a Schottky metal placed in the first window and disposed on the substrate;
a final metal disposed on the nitride layer and the Schottky metal and having a second window exposing the Schottky metal; and
an encapsulating layer (e.g., a polymethyl-methacrylate (PMMA) layer) encapsulating the second window.

Embodiment 2

The hydrogen sensor according to embodiment 1, wherein the encapsulating layer covers a part of the Ohmic metal and a part of the final metal.

Embodiment 3

The hydrogen sensor according to any of embodiments 1-2, wherein the encapsulating layer fills the second window and is in contact with the Schottky metal.

Embodiment 4

The hydrogen sensor according to any of embodiments 1-3, wherein the Schottky metal is in contact with a side surface and a top surface of the nitride layer.

Embodiment 5

The hydrogen sensor according to any of embodiments 1-4, wherein the final metal is in contact with a side surface and a top surface of the Schottky metal.

Embodiment 6

The hydrogen sensor according to any of embodiments 1-5, wherein the Ohmic metal and the Schottky metal are disposed on the same plane of the substrate.

Embodiment 7

The hydrogen sensor according to any of embodiments 1-6, wherein the Schottky metal comprises platinum (Pt).

Embodiment 8

The hydrogen sensor according to any of embodiments 1-7, wherein the substrate comprises a sapphire layer, a GaN layer on the sapphire layer, and an AlGaN layer on the GaN layer.

Embodiment 9

The hydrogen sensor according to embodiment 8, wherein the GaN layer is a c-plane GaN layer and the AlGaN layer is an $Al_xGa_{1-x}N$ layer, where x is in a range of 0 to 1.

Embodiment 10

The hydrogen sensor according to any of embodiments 1-9, wherein the nitride layer is a $SiN_x$ layer.

Embodiment 11

The hydrogen sensor according to embodiment 10, wherein the $SiN_x$ layer is in contact with a side surface and a top surface of the Ohmic metal.

Embodiment 12

The hydrogen sensor according to any of embodiments 1-11, wherein the Ohmic metal comprises a titanium (Ti) layer, an aluminum (Al) layer, a nickel (Ni) layer, and a gold (Au) layer.

Embodiment 13

The hydrogen sensor according to any of embodiments 1-12, wherein the final metal comprises a Ti layer and an Au layer.

Embodiment 14

The hydrogen sensor according to embodiment 8, wherein the encapsulating layer is in contact with the AlGaN layer.

Embodiment 15

The hydrogen sensor according to embodiment 3, wherein a first width of the first window is larger than a second width of the second window.

Embodiment 16

The hydrogen sensor according to any of embodiments 1-15, wherein the substrate comprises at least one of sapphire, SiC, and silicon.

Embodiment 17

A Schottky diode, comprising:
a substrate;
an Ohmic metal disposed on an Ohmic contact area of the substrate;
a nitride layer disposed on the substrate and having a window exposing a Schottky contact area of the substrate;
a Schottky metal disposed on the Schottky contact area of the substrate;
a final metal connected to the Schottky metal; and
a polymer encapsulant disposed directly on the Schottky metal.

Embodiment 18

The Schottky diode according to embodiment 17, wherein the Schottky metal is platinum.

Embodiment 19

The Schottky diode according to any of embodiments 17-18, wherein the substrate comprises a GaN layer and an AlGaN layer on the GaN layer.

Embodiment 20

The Schottky diode according to any of embodiments 17-19, wherein the polymer encapsulant covers the Ohmic metal, the nitride layer, the Schottky metal, the final metal, and the substrate.

Embodiment 21

The Schottky diode according to any of embodiments 19-20, wherein the polymer encapsulant is in direct physical contact with the AlGaN layer of the substrate.

Embodiment 22

The Schottky diode according to any of embodiments 17-21, wherein the polymer encapsulant comprises at least one of polymethyl-methacrylate (PMMA), polyimide, polycarbonate, and benzocyclobutene (BCB).

Embodiment 23

A method for manufacturing a hydrogen sensor, comprising:
providing a substrate;
forming an Ohmic metal on an Ohmic contact area of the substrate;
depositing a nitride layer (e.g., $SiN_x$ layer) on the substrate and the Ohmic metal;
forming a first window exposing a Schottky contact area of the substrate by removing the nitride layer on the substrate;
forming a Schottky metal on the Schottky contact area of the substrate;
forming a final metal on the Schottky metal; and
forming an encapsulating layer (e.g., a polymethyl-methacrylate (PMMA) layer) encapsulating the Schottky metal.

Embodiment 24

The method according to embodiment 23, wherein the encapsulating layer is in direct physical contact with the Schottky metal.

Embodiment 25

The method according to any of embodiments 23-24, wherein forming the encapsulating layer comprises spinning PMMA on the Schottky metal, the final metal, and the Ohmic metal, and removing the PMMA on the final metal and the Ohmic metal.

Embodiment 26

The method according to any of embodiments 23-25, wherein forming the Ohmic metal comprises depositing Ti/Al/Ni/Au layers on the substrate, annealing under nitrogen ($N_2$) ambient, and removing the Ti/Al/Ni/Au layers except the Ohmic contact area of the substrate.

Embodiment 27

The method according to any of embodiments 23-26, wherein forming the Schottky metal comprises depositing Pt by e-beam evaporation.

Embodiment 28

The method according to any of embodiments 23-27, wherein the final metal comprises Ti/Au interconnection contacts and the final metal is formed by e-beam deposition.

A greater understanding of the present invention and of its many advantages may be had from the following example, given by way of illustration. The following example is illustrative of some of the methods, applications, embodiments, and variants of the present invention. It is, of course, not to be considered as limiting the invention. Numerous changes and modifications can be made with respect to the invention.

Example 1

Figure 3:
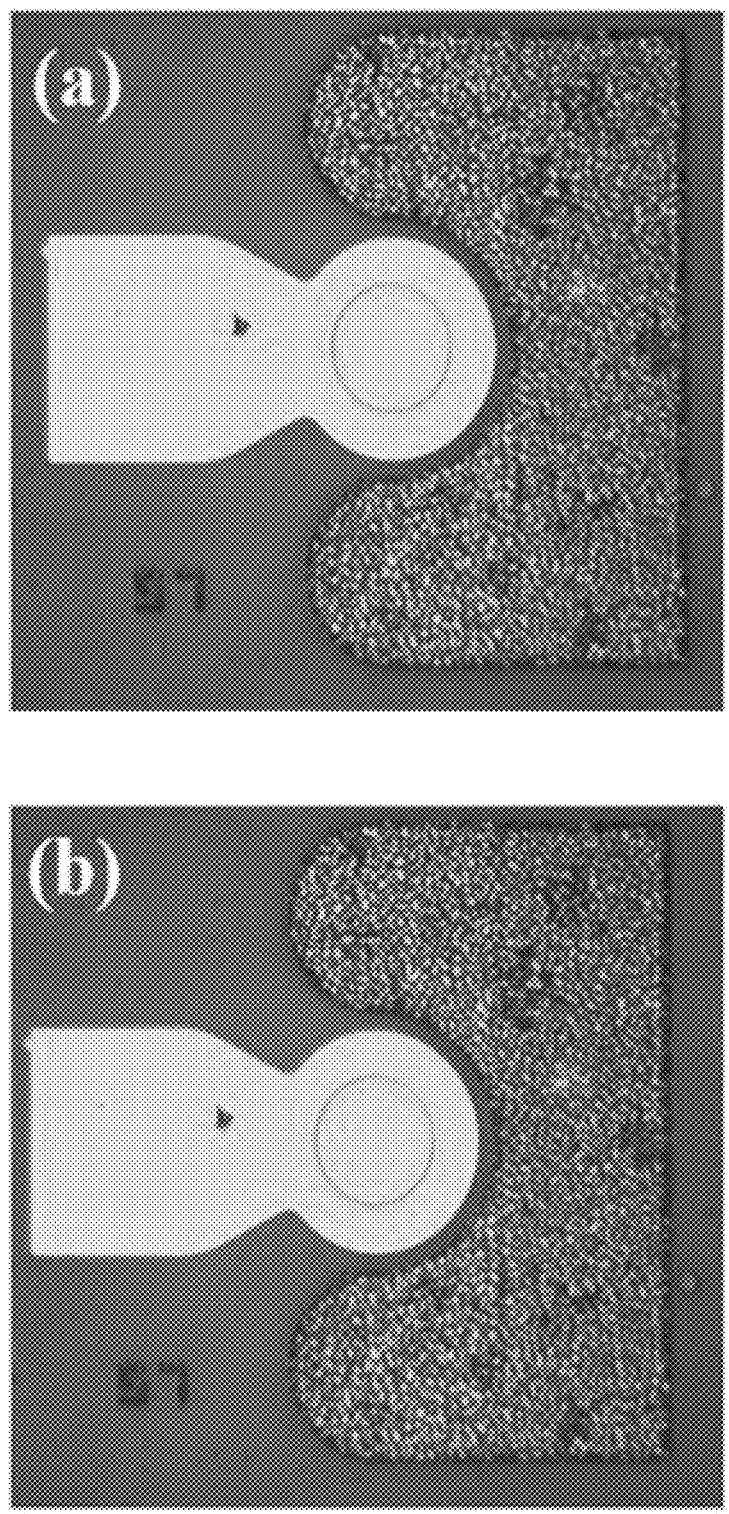
FIG. 3 shows optical microscope images of a hydrogen sensor according to an embodiment of the subject invention before and after thermal cycle.

Hydrogen sensors including Schottky diodes were manufactured such that they included the PMMA encapsulation as discussed herein. To test the stability of the encapsulation, devices were cycled 50 times between 25-100° C., with the diodes held for 1 minute at each extreme of this temperature range. FIG. 3 shows an optical microscope image after 50 cycles to 100° C., with no change in appearance of the sensor. This shows that over this temperature range, the PMMA is stable. Current-voltage (I-V) characteristics of both the uncoated and encapsulated Schottky diodes were measured at 25° C. using an Agilent 4156C parameter analyzer with the diodes in a gas test chamber in ambient of $N_2$ or 0.01-4% $H_2$ (corresponding to 100-40,000 ppm) dry hydrogen in nitrogen or the same concentrations of hydrogen bubbled through water to produce 100% relative humidity.

Figure 4A:
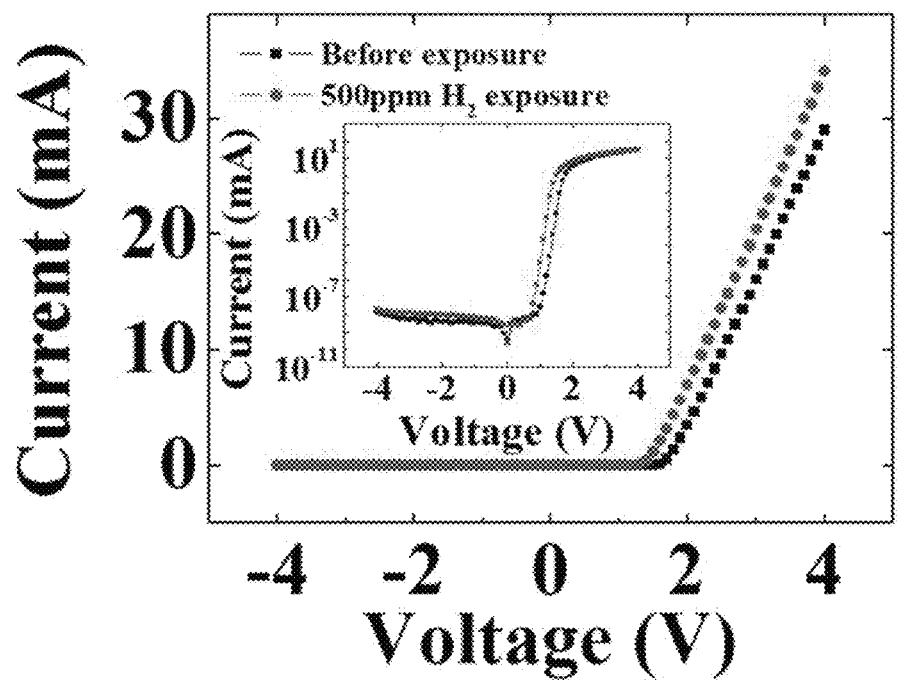
FIG. 4(a) shows I-V characteristics of an un-encapsulated hydrogen sensor before and after 500 ppm $H_2$ exposure.
Figure 4B:
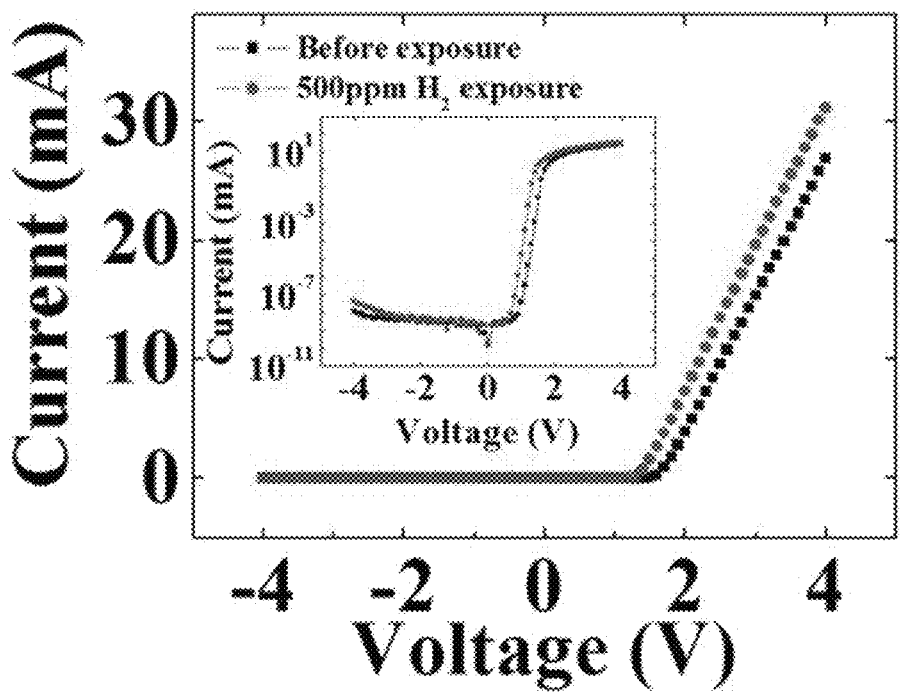
FIG. 4(b) shows I-V characteristics of an encapsulated hydrogen sensor according to an embodiment of the subject invention before and after 500 ppm $H_2$ exposure.

FIGS. 4(a) and 4(b) show I-V characteristics of an un-encapsulated hydrogen sensor and an encapsulated hydrogen sensor, respectively, before and after exposure to 500 ppm $H_2$ in $N_2$ on a linear scale with the same data on a log scale in the inset. Referring to FIGS. 4(a) and 4(b), the I-V characteristics were unaffected by the presence of the PMMA and the same absolute and temporal characteristics were obtained when detecting dry hydrogen.

Figure 5A:
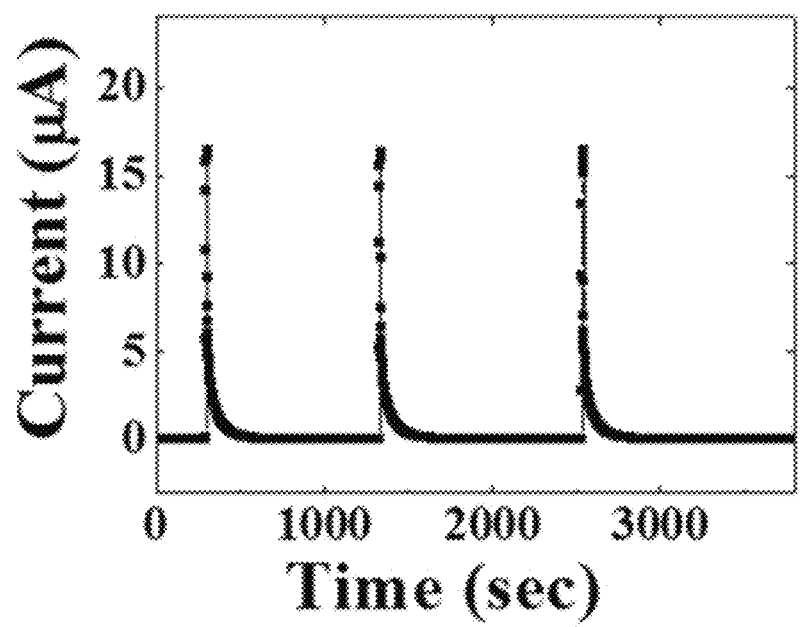
FIG. 5(a) shows a time response of an un-encapsulated hydrogen sensor for dry 500 ppm hydrogen exposure.
Figure 5B:
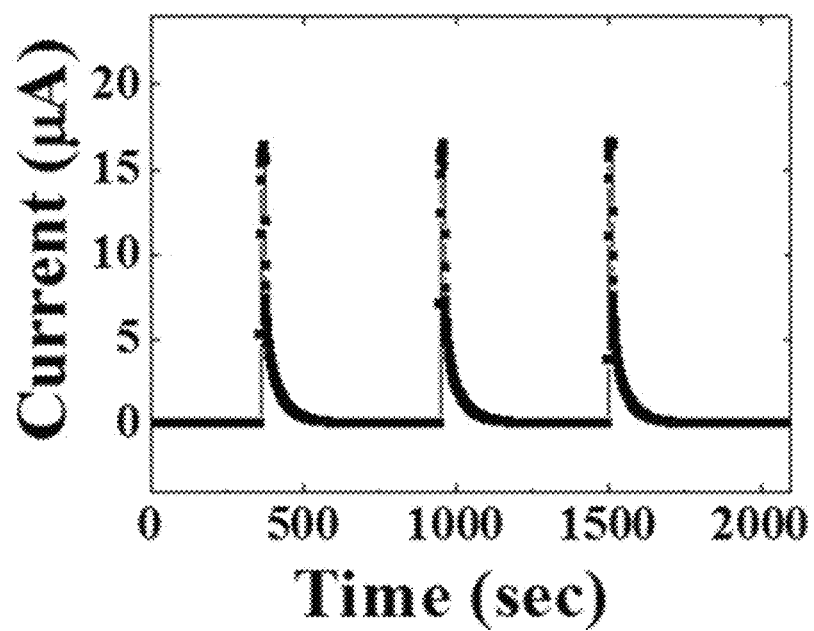
FIG. 5(b) shows a time response of an encapsulated hydrogen sensor according to an embodiment of the subject invention for dry 500 ppm hydrogen exposure.

FIGS. 5(a) and 5(b) show time responses of an un-encapsulated hydrogen sensor and an encapsulated hydrogen sensor according to an embodiment of the subject invention, respectively. The time responses of the forward current at 1.3 V of the un-encapsulated hydrogen sensor of FIG. 5(a) and the encapsulated hydrogen sensor of FIG. 5(b) were measured after cycled exposure from $N_2$ to 500 ppm $H_2$ in $N_2$. The hydrogen was introduced into the test chamber for 15 secs each time and then $N_2$ was reintroduced. Referring to FIGS. 5(a) and 5(b), the absolute current signal and recovery characteristics were unaffected by the presence of the PMMA, and the same absolute and temporal characteristics were obtained when detecting dry hydrogen.

Figure 6A:
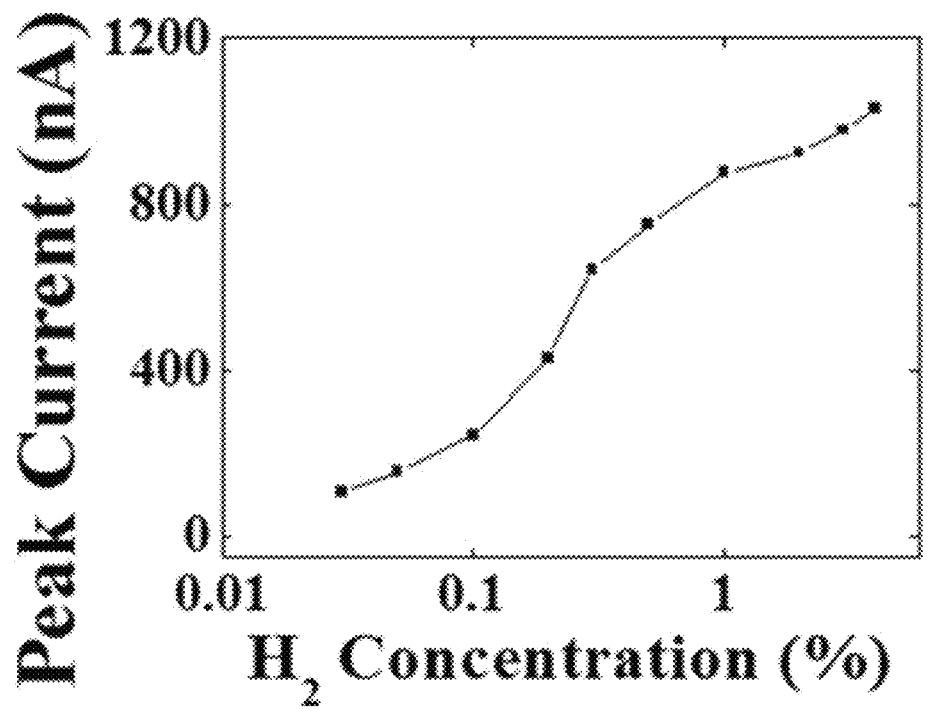
FIG. 6(a) shows a current response with respect to $H_2$ concentration of an un-encapsulated hydrogen sensor.
Figure 6B:
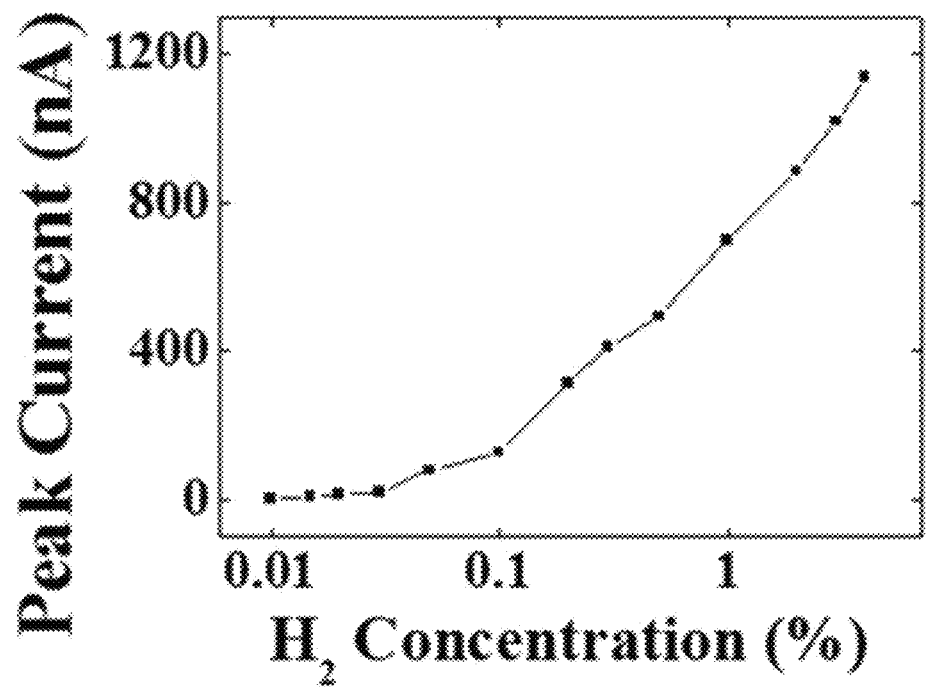
FIG. 6(b) shows a current response with respect to $H_2$ concentration of an encapsulated hydrogen sensor according to an embodiment of the subject invention.

FIG. 6(a) shows a current response with respect to $H_2$ concentration of an un-encapsulated hydrogen sensor. FIG. 6(b) shows a current response with respect to $H_2$ concentration of an encapsulated hydrogen sensor according to an embodiment of the subject invention. Referring to FIGS. 6(a) and 6(b), the current responses of the sensors as a function of hydrogen concentration were not affected by the PMMA encapsulant. There was no significant difference in response for un-encapsulated versus encapsulated sensors.

Figure 7:
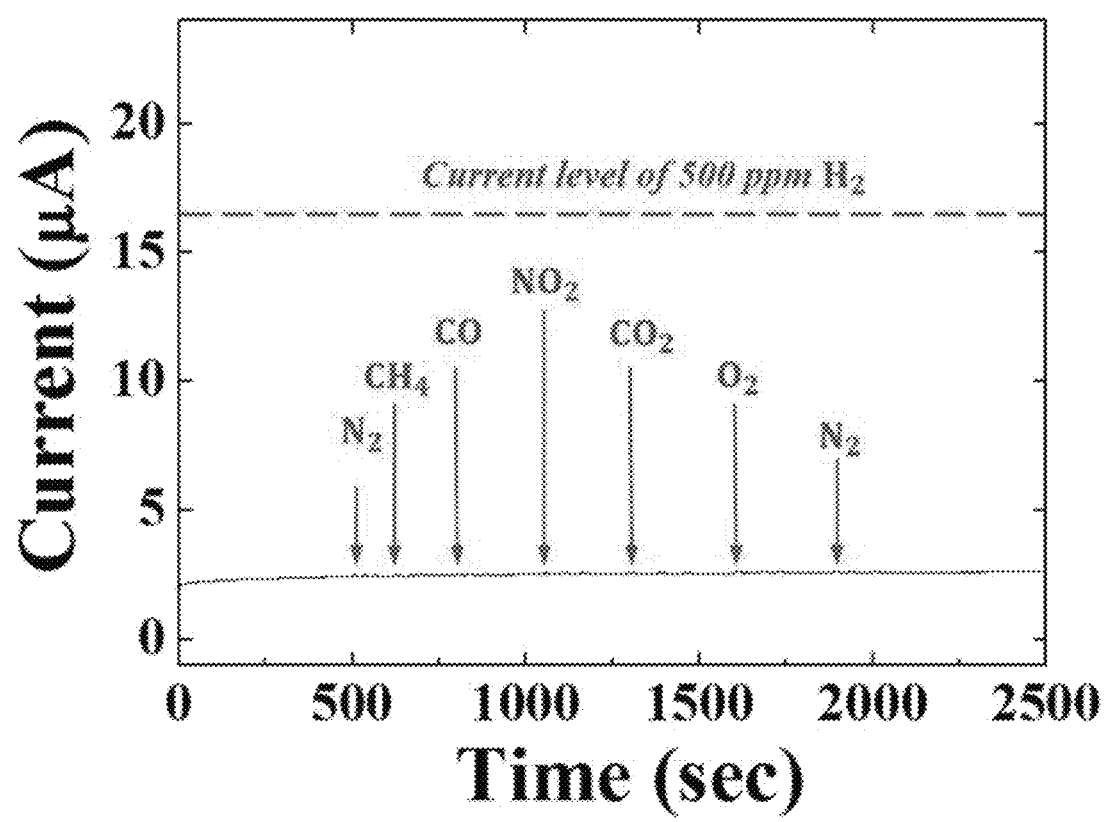
FIG. 7 shows selective characteristics with respect to $H_2$ of an encapsulated hydrogen sensor according to an embodiment of the subject invention.

FIG. 7 shows selective characteristics with respect to $H_2$ of an encapsulated hydrogen sensor according to an embodiment of the subject invention. Referring to FIG. 7, the PMMA encapsulated sensors were completely selective to hydrogen detection, and did not respond to the other gases sequentially introduced for three cycles into the test chamber, namely $CH_4$ (4% in $N_2$), CO (0.1% in $N_2$), $NO_2$ (0.05% in $N_2$), $CO_2$ (10% in $N_2$), and $O_2$ (100%). The concentrations of gases were chosen in the range of U.S. health exposure limits by national institute for occupational safety and health. $H_2$ molecules (0.298 nm) have the smallest kinetic diameter among those gases including $CH_4$ (0.380 nm), CO (0.376 nm), $NO_2$ (0.340 nm), $CO_2$ (0.330 nm) and $O_2$ (0.346 nm); hence, there exists the most possibility for $H_2$ to penetrate the PMMA layer. The small transients upon introduction of each gas are due to the pressure variations at the surface of the sensor as each gas is directed towards it.

Figure 8:
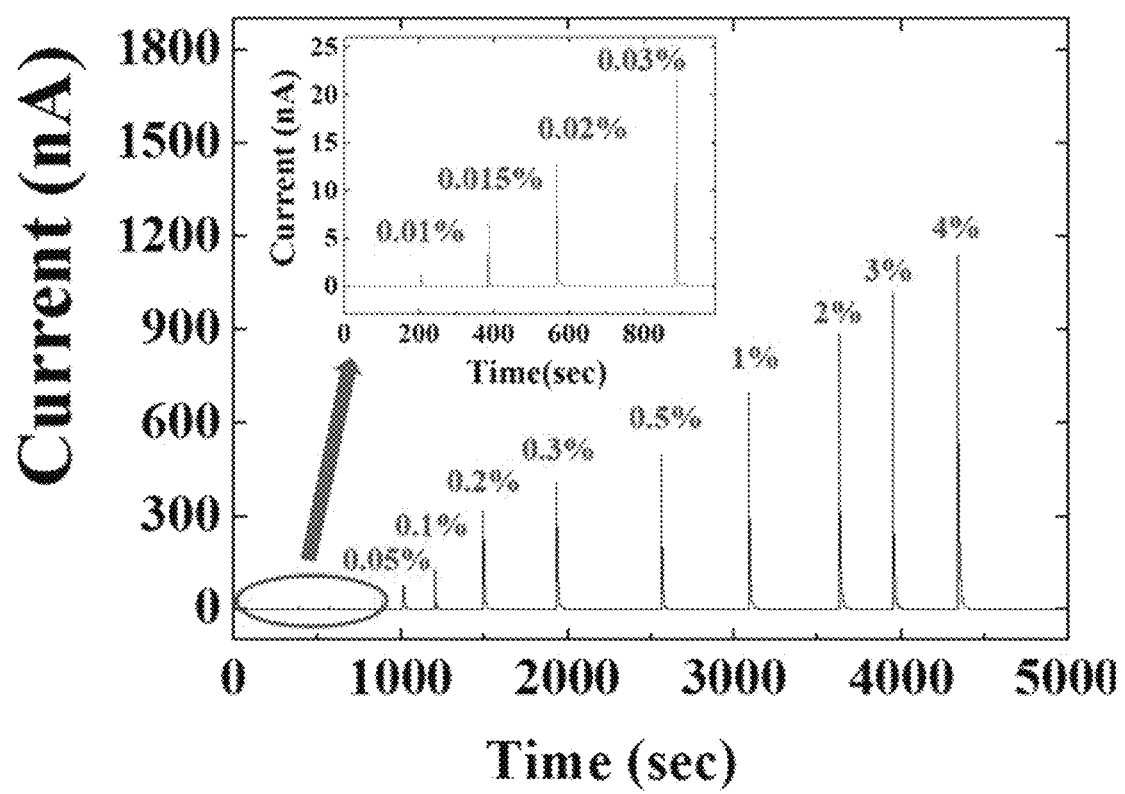
FIG. 8 shows a current change with respect to exposure time of an encapsulated hydrogen sensor according to an embodiment of the subject invention.

FIG. 8 shows the current change of encapsulated diodes as a function of time for exposure to different concentrations (0.01-4% by volume) of dry $H_2$ in $N_2$. The forward bias voltage was held constant at 1.3 V. The different hydrogen concentrations were introduced for 15 secs each and then the test chamber was purged with $N_2$ prior to introduction of the next hydrogen concentration. The sensors begin to respond at a hydrogen concentration of 0.01% or 100 ppm. The results for dry $H_2$ were independent of whether the sensors were encapsulated with the PMMA.

Figure 9A:
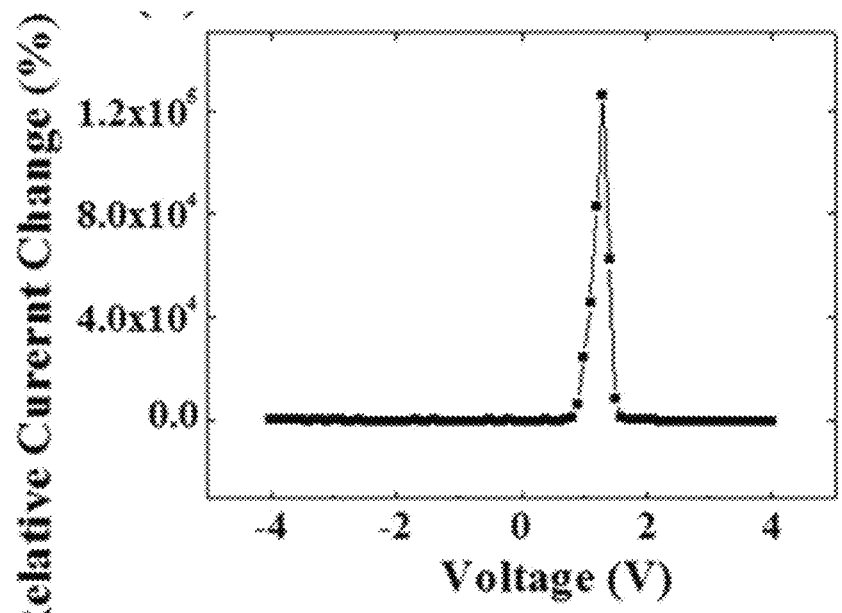
FIG. 9(a) shows a relative current change of an unheated encapsulated hydrogen sensor according to an embodiment of the subject invention.
Figure 9B:
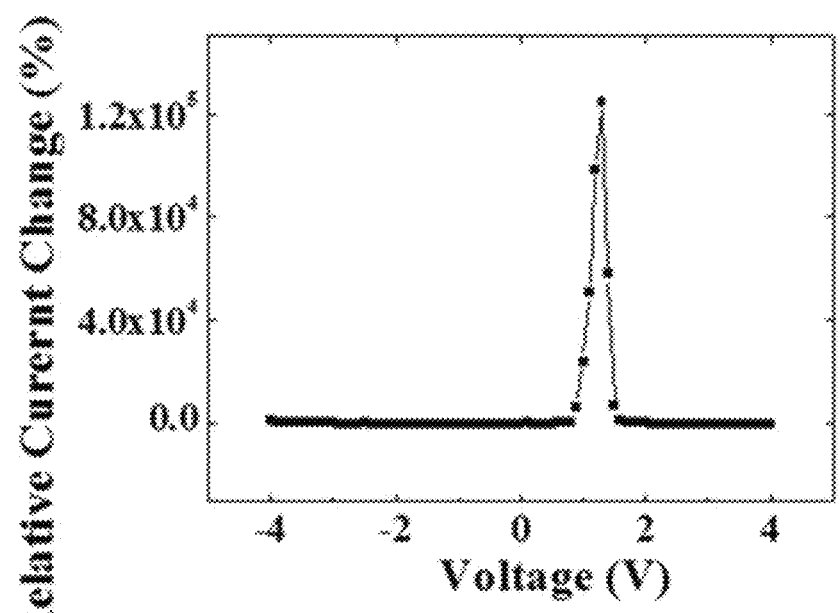
FIG. 9(b) shows a relative current change of a thermally cycled encapsulated hydrogen sensor according to an embodiment of the subject invention.

FIG. 9(a) shows a relative current change of an unheated encapsulated hydrogen sensor according to an embodiment of the subject invention. FIG. 9(b) shows a relative current change of a thermally cycled encapsulated hydrogen sensor according to an embodiment of the subject invention. Referring to FIGS. 9(a) and 9(b), the encapsulation was not affected by thermal cycling, where the dry $H_2$ sensitivity of the Pt—AlGaN/GaN diodes is shown for unheated and thermally cycled devices. FIGS. 9(a) and 9(b) show the percentage current change as a function of bias (negative voltage corresponds to reverse bias and positive voltage to forward bias) of the sensors for exposure to 500 ppm of $H_2$. The results are similar for encapsulated diodes that had not been heated after the PMMA was applied and the PMMA-coated diodes that had been cycled 50 times from 25° C. to 100° C. before return to 25° C. and exposure to the 500 ppm $H_2$. Both of the sensors show the same percentage increase in current of ~$1.2 \times 10^5$% at 1.3V forward bias when exposed to 500 ppm $H_2$ relative to the value in pure $N_2$. The result confirms the fact that thermal cycling over the range from room temperature to 100° C. had no effect on the sensor performance.

Figure 10:
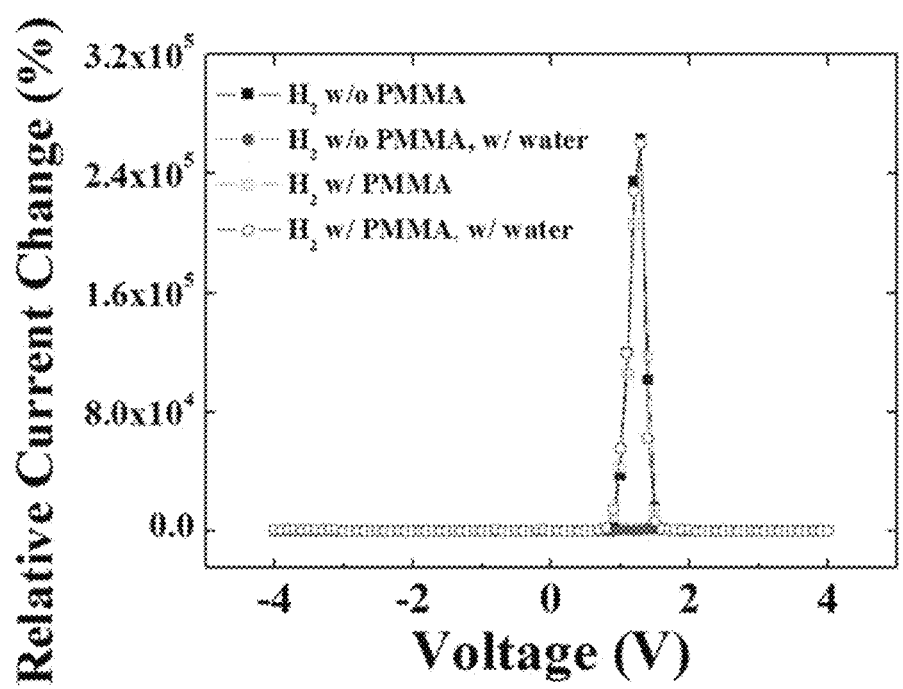
FIG. 10 shows a relative current change with respect to water of un-encapsulated and encapsulated hydrogen sensors.

FIG. 10 shows the relative percentage current change of both bare (e.g., un-encapsulated) and encapsulated diodes as a function of bias voltage for exposure to 500 ppm $H_2$ either dry or with 100% humidity. The bare sensors suffered a major decrease in sensitivity in the presence of the water vapor content in the hydrogen relative to dry conditions. Secondly, the PMMA encapsulation is completely successful in eliminating this decrease due to the increased humidity level, while still retaining the same absolute detection sensitivity (~$2.8 \times 10^5$% at low forward bias voltage).

Figure 11A:
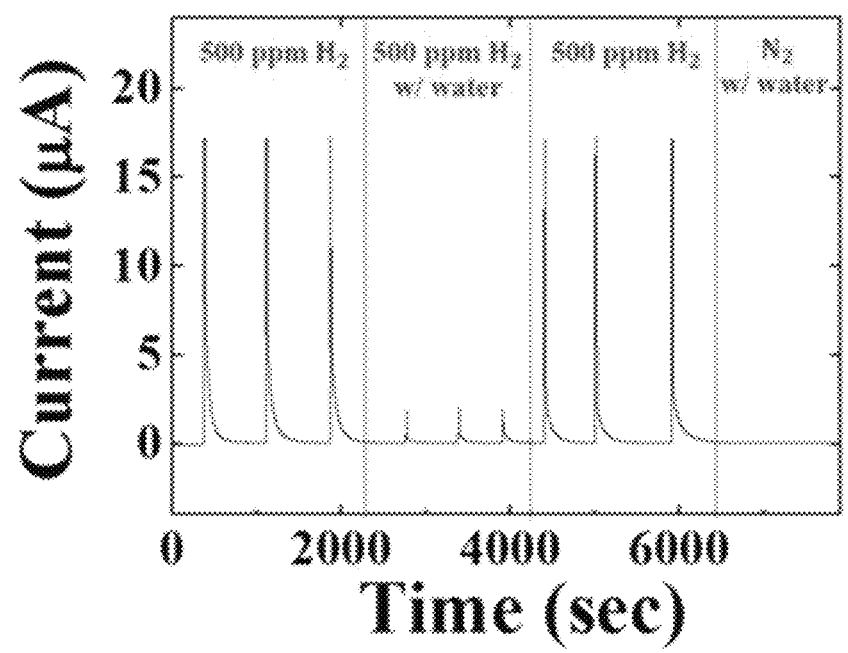
FIG. 11(a) shows a response of an un-encapsulated hydrogen sensor.
Figure 11B:
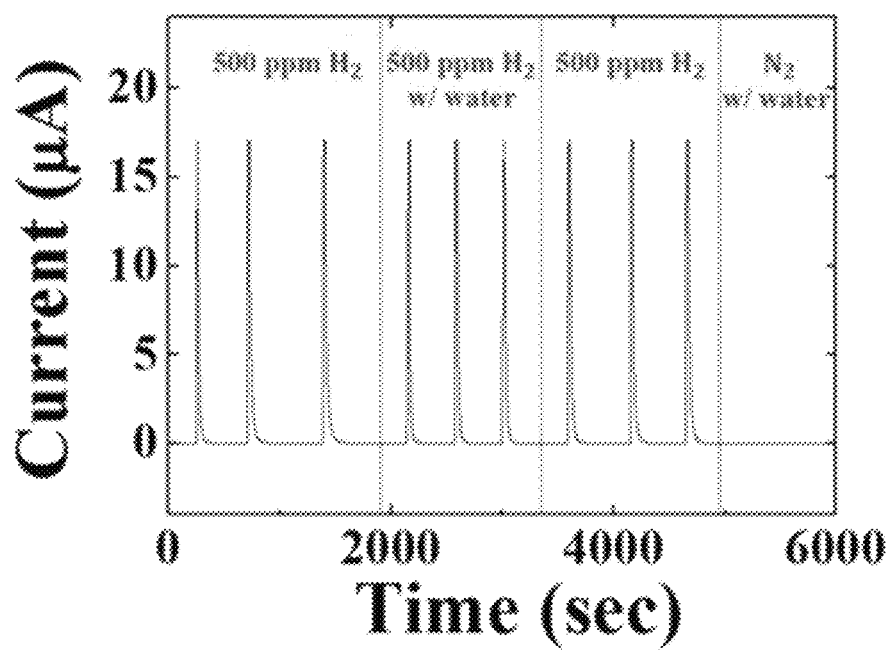
FIG. 11(b) shows a response of an encapsulated hydrogen sensor according to an embodiment of the subject invention.

FIGS. 11(a) and 11(b) show the responses of bare (e.g., un-encapsulated) and encapsulated diodes to three cycles of 500 ppm $H_2$, followed by switching to the wet $H_2$ for 3 cycles and then back to the dry H$_2$. The decrease in response of the bare diode was measured when the wet H$_2$ is introduced. By sharp contrast, the PMMA encapsulated diodes show the same response to both dry and wet H$_2$. Finally, 3 cyclic exposures of wet N$_2$ were introduced to both devices, but the responses were nominal. While PMMA has low permeability coefficients for oxygen and moisture, some other common polymers have even lower values, (e.g., poly(vinyl chloride), poly(ethylene) and poly(trifluoro chloroethylene)) and are also candidates as encapsulants, although ease of application and compatibility with semiconductor surfaces must be considered.

According to above example, while un-encapsulated Pt—AlGaN/GaN diode sensors suffer a major decrease in sensitivity in the presence of the water vapor content in the hydrogen [35], the encapsulated sensor using PMMA is successful in eliminating this decrease due to the increased humidity level, while still retaining the same absolute detection sensitivity. Other common polymers such as poly(vinyl chloride), poly(ethylene) and poly(trifluoro chloroethylene) have even lower permeability coefficients for oxygen and moisture and could also be used for hydrogen sensor encapsulation. The example shows that PMMA can be repeatedly thermally cycled between room temperature and 100° C. without any degradation of moisture barrier properties on the Pt—AlGaN/GaN hydrogen sensors. This is an effective solution to deploying the sensors in an ambient environment in which the humidity is likely to vary with time.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. J. Kim, I. Moon, Strategic design of hydrogen infrastructure considering cost and safety using multiobjective optimization, Int. J. Hydrogen Energy, 33 (2008), pp. 5887-5896
2. G. R. Astbury, S. J. Hawksworth, Spontaneous ignition of hydrogen leaks: A review of postulated mechanisms, Int. J. Hydrogen Energy, 32 (2007), pp. 2178-2185
3. T. Hübert, L. Boon-Brett, V. Palmisano, M. A. Bader, Developments in gas sensor technology for hydrogen safety, Int. J. Hydrogen Energy, 39 (2014), pp. 20474-20483
4. O. Weidemann, M. Hermann, G. Steinhoff, H. Wingbrant, A. L. Spetz, M. Stutzmann, M. Eickoff, Influence of surface oxides on hydrogen-sensitive Pd:GaN Schottky diodes, Appl. Phys. Lett., 83 (2003), pp. 773-775
5. J. Song, W. Lu, J. S. Flynn, G. R. Brandes, AlGaN/GaN Schottky diode hydrogen sensor performance at high temperature with different catalytic metals, Solid-State Electron., 49 (2005), pp. 1330-1334
6. L. Voss, B. P. Gila, S. J. Pearton, H. Wang, F. Ren, Characterization of bulk GaN rectifiers for hydrogen gas sensing, J. Vac. Sci. Technol., B, 23 (2005), pp. 2373-2377
7. H. Wang, T. J. Anderson, F. Ren, C. Li, Z. Low, J. Lin, B. P. Gila, S. J. Pearton, A. Osinsky, A. Dabiran, Robust detection of hydrogen using differential AlGaN/GaN high electron mobility transistor sensing diodes, Appl. Phys. Lett., 89 (2006), pp. 2111-2113
8. S. Hung, C. Chang, C. Hsu, B. H. Chu, C. F. Lo, C. Hsu, S. J. Pearton, M. R. Holzworth, P. G. Whiting, N. G. Rudawski, K. S. Jones, A. Dabiran, P. Chow, F. Ren, SnO$_2$ functionalized AlGaN/GaN high electron mobility transistor for hydrogen sensing applications, Int. J. Hydrogen Energy, 37 (2012), pp. 13783-13788
9. H. T. Wang, B. S. Kang, F. Ren, L. C. Tien, P. W. Sadik, D. P. Norton, S. J. Pearton, J. Lin, Hydrogen-selective sensing at room temperature with ZnO nanorods, Appl. Phys. Lett., 86 (2005), pp. 243503
10. S. Jang, J. Kim, K. H. Baik, Enhanced Hydrogen Detection Sensitivity of Semipolar ($11\bar{2}2$) GaN Schottky Diodes by Surface Wet Etching on Schottky Contact, J. Electrochem. Soc., 163 (2016), pp. B456-B459
11. K. H. Baik, J. Kim, S. Jang, Improved GaN Based Hydrogen Sensors, ECS Trans., 72 (2016), pp. 23-28
12. S. Jang, P. Son, J. Kim, S. Lee, K. H. Baik, Hydrogen sensitive Schottky diode using semipolar ($11\bar{2}2$) AlGaN/GaN heterostructures, Sens. Actuators, B, 222 (2016), pp. 43-47
13. H. Kim, K. H. Baik, F. Ren, S. J. Pearton, S. Jang, (Invited) Hydrogen Sensing Characteristics of Gallium Nitrides with Various Crystal Planes, ECS Trans., 61 (2014), pp. 353-373
14. K. H. Baik, H. Kim, S. Lee, E. Lim, S. J. Pearton, F. Ren, S. Jang, Hydrogen sensing characteristics of semipolar ($11\bar{2}2$) GaN Schottky diodes, Appl. Phys. Lett., 104 (2014), pp. 072103
15. H. Kim, W. Lim, J. Lee, S. J. Pearton, F. Ren, S. Jang, Highly sensitive AlGaN/GaN diode-based hydrogen sensors using platinum nanonetworks, Sens. Actuators, B, 164 (2012), pp. 64-68
16. Y. Wang, F. Ren, W. Lim, S. J. Pearton, K. H. Baik, S. Hwang, Y. G. Seo, S. Jang, Hydrogen sensing characteristics of non-polar a-plane GaN Schottky diodes, Curr. Appl. Phys., 10 (2010), pp. 1029-1032
17. K. Matsuo, N. Negoro, J. Kotani, T. Hashizume, H. Hasegawa, Pt Schottky diode gas sensors formed on GaN and AlGaN/GaN heterostructure, Appl. Surf. Sci., 244 (2005), pp. 273-276
18. H. Hasegawa, M. Akazawa, Hydrogen sensing characteristics and mechanism of Pd/AlGaN/GaN Schottky diodes subjected to oxygen gettering, J. Vac. Sci. Technol., B, 25 (2007), pp. 1495-1503
19. A. Zhong, T. Sasaki, K. Hane, Platinum/porous GaN nanonetwork metal-semiconductor Schottky diode for room temperature hydrogen sensor, Sens. Actuators, A, 209 (2014), pp. 52-56
20. H. Kim, S. Jang, AlGaN/GaN HEMT based hydrogen sensor with platinum nanonetwork gate electrode, Curr. Appl. Phys., 13 (2013), pp. 1746-1750
21. J. Song, W. Lu, J. S. Flynn, G. R. Brandes, Pt—AlGaN/GaN Schottky diodes operated at 800° C. for hydrogen sensing, Appl. Phys. Lett., 87 (2005), pp. 3501-3503
22. B. S. Kang, F. Ren, B. P. Gila, C. R. Abernathy, S. J. Pearton, AlGaN/GaN-based metal-oxide-semiconductor diode-based hydrogen gas sensor, Appl. Phys. Lett., 84 (2004), pp. 1123-1125
23. W. Lim, J. S. Wright, B. P. Gila, J. L. Johnson, A. Ural, T. Anderson, F. Ren, S. J. Pearton, Room temperature hydrogen detection using Pd-coated GaN nanowires, Appl. Phys. Lett., 93 (2008), pp. 72109

24. Y. Irokawa, Hydrogen interaction with GaN metal-insulator-semiconductor diodes, Phys. B, 407 (2012), pp. 2957-2959
25. Y. Wang, F. Ren, U. Zhang, Q. Sun, C. D. Yerino, T. S. Ko, Y. S. Cho, I. H. Lee, J. Han, S. J. Pearton, Improved hydrogen detection sensitivity in N-polar GaN Schottky diodes, Appl. Phys. Lett., 94 (2009), pp. 212108-212110
26. T. J. Anderson, H. T. Wang, B. S. Kang, F. Ren, S. J. Pearton, A. Osinsky, A. Dabiran, P. P. Chow, Effect of bias voltage polarity on hydrogen sensing with AlGaN/GaN Schottky diodes, Appl. Surf. Sci., 255 (2008), pp. 2524-2526
27. Y. Liu, J. Yu, W. M. Tang, P. T. Lai, On the voltage dependence of sensitivity for Schottky-type gas sensor, Appl. Phys. Lett., 105 (2014), pp. 223503
28. C. Chen, H. Chen, I. Liu, H. Liu, P. Chou, J. Liou, W. Liu, Enhancement of hydrogen sensing performance of a GaN-based Schottky diode with a hydrogen peroxide surface treatment, Sens. Actuators, B, 211 (2015), pp. 303-309
29. X. Yu, C. Li, Z. N. Low, J. Lin, T. J. Anderson, H. T. Wang, F. Ren, Y. L. Wang, C. Y. Chang, S. J. Pearton, C. H. Hsu, A. Osinsky, A. Dabiran, P. Chow, C. Balaban, J. Painter, Wireless hydrogen sensor network using AlGaN/GaN high electron mobility transistor differential diode sensors, Sens. Actuators, B, 135 (2008), pp. 188-194
30. K. H. Baik, J. Kim, S. Jang, Highly sensitive nonpolar a-plane GaN based hydrogen diode sensor with textured active area using photo-chemical etching, Sens. Actuators, B, 238 (2017), pp. 462-467
31. A. Zhong, T. Sasaki, K. Hane, Comparative study of Schottky diode type hydrogen sensors based on a honeycomb GaN nanonetwork and on a planar GaN film, Int. J. Hydrogen Energy, 39 (2014), pp. 8564-8575
32. Y. Tsai, K. Lin, H. Chen, I. Liu, C. Hung, T. Chen, T. Tsai, L. Chen, K. Chu, W. Liu, Hydrogen sensing properties of a Pt-oxide-GaN Schottky diode, J. Appl. Phys., 104 (2008), pp. 024515
33. Y. Irokawa, Interface states in metal-insulator-semiconductor Pt—GaN diode hydrogen sensors, J. Appl. Phys., 113 (2013), pp. 026104
34. C. Lo, S. Tan, C. Wei, J. Tsai, K. Hsu, W. Lour, Unidirectional sensing characteristics of structured Au—GaN—Pt diodes for differential-pair hydrogen sensors, Int. J. Hydrogen Energy, 37 (2012), pp. 18579-18587
35. Y. Xi, L. Liu, Y. Hwang, O. Phillips, F. Ren, S. J. Pearton, J. Kim, C. Hsu, C. Lo, J. W. Johnson, Study of hydrogen detection response time with Pt-gated diodes fabricated on AlGaN/GaN heterostructure, J. Vac. Sci. Technol., B, 31 (2013), pp. 032202
36. C. F. Lo, C. Y. Chang, B. H. Chu, S. J. Pearton, A. Dabiran, P. P. Chow, F. Ren, Effect of humidity on hydrogen sensitivity of Pt-gated AlGaN/GaN high electron mobility transistor based sensors, *Appl. Phys. Lett.,* 96 (2010), pp. 232106
37. S. Das, S. Majumdar, R. Kumar, A. Chakraborty, A. Bag, D. Biswas, Simplified gas sensor model based on AlGaN/GaN heterostructure Schottky diode, AIP Conf. Proc., 1675 (2015), pp. 020014
38. B. S. Kang, S. Kim, F. Ren, B. P. Gila, C. R. Abernathy, S. J. Pearton, Comparison of MOS and Schottky W/Pt—GaN diodes for hydrogen detection, Sens. Actuators, B, 104 (2005), pp. 232-236
39. J. Hong, S. Lee, J. Seo, S. Pyo, J. Kim, T. Lee, A highly sensitive hydrogen sensor with gas selectivity using a PMMA membrane-coated Pd nanoparticle/single-layer graphene hybrid, ACS Appl. Mater. Interfaces, 7 (2015), pp. 3554-3561
40. R. J. Ashley, Permeability and Plastics Packaging in Polymer Permeability, edited by J. Comyn, Elsevier Applied Science Publishers, London, (1985), pp. 269-305

What is claimed is:

1. A hydrogen sensor, comprising:
a substrate;
an Ohmic metal disposed on the substrate;
a nitride layer disposed on the substrate and having a first window exposing the substrate;
a Schottky metal placed in the first window and disposed on the substrate;
a final metal disposed on the nitride layer and the Schottky metal and having a second window exposing the Schottky metal; and
a polymethyl-methacrylate (PMMA) layer encapsulating the second window.

2. The hydrogen sensor according to claim 1, wherein the PMMA layer covers a part of the Ohmic metal and a part of the final metal.

3. The hydrogen sensor according to claim 2, wherein the PMMA layer fills the second window and is in contact with the Schottky metal.

4. The hydrogen sensor according to claim 3, wherein the Schottky metal is in contact with a side surface and a top surface of the nitride layer.

5. The hydrogen sensor according to claim 4, wherein the final metal is in contact with a side surface and a top surface of the Schottky metal.

6. The hydrogen sensor according to claim 3, wherein the Ohmic metal and the Schottky metal are disposed on the same plane of the substrate.

7. The hydrogen sensor according to claim 6, wherein the Schottky metal comprises platinum (Pt).

8. The hydrogen sensor according to claim 7, wherein the substrate comprises a sapphire layer, a GaN layer on the sapphire layer, and an AlGaN layer on the GaN layer.

9. The hydrogen sensor according to claim 8, wherein the GaN layer is a c-lane GaN layer and the AlGaN layer is an $Al_xGa_{1-x}N$ layer, where x is in a range of 0 to 1.

10. The hydrogen sensor according to claim 8, wherein the Ohmic metal comprises a titanium (Ti) layer, an aluminum (Al) layer, a nickel (Ni) layer, and a gold (Au) layer.

11. The hydrogen sensor according to claim 8, wherein the final metal comprises a Ti layer and an Au layer.

12. The hydrogen sensor according to claim 3, wherein a first width of the first window is larger than a second width of the second window.

13. The hydrogen sensor according to claim 3, wherein the substrate comprises at least one of sapphire, SiC, and silicon.

* * * * *